United States Patent [19]

Chorvat

[11] 4,329,295

[45] May 11, 1982

[54] 24-CYCLOPROPYLCHOLENE-3β, 22-DIOLS AND ESTERS THEREOF

[75] Inventor: Robert J. Chorvat, Arlington Heights, Ill.

[73] Assignee: G. D. Searle & Co., Skokie, Ill.

[21] Appl. No.: 278,276

[22] Filed: Jun. 29, 1981

[51] Int. Cl.³ .............................................. C07J 9/00
[52] U.S. Cl. ................................................. 260/397.2
[58] Field of Search ..................................... 260/397.2

[56] References Cited

U.S. PATENT DOCUMENTS 4,292,249  9/1981  Nishikawa et al. ............. 260/397.2
4,292,250  9/1981  DeLuca et al. .................. 260/397.2

*Primary Examiner*—Elbert L. Roberts
*Attorney, Agent, or Firm*—W. Dennis Drehkoff; James G. Passe'

[57] ABSTRACT

24-Cyclopropylcholene-3β, 22-diols and esters thereof which control serum cholesterol levels and their preparation are disclosed.

8 Claims, No Drawings

24-CYCLOPROPYLCHOLENE-3β, 22-DIOLS AND ESTERS THEREOF

BACKGROUND OF THE INVENTION

This invention relates to 24 Cyclopropylcholene-3β,22-diols and esters thereof. More particularly, this invention relates to useful chemical compounds of the formula

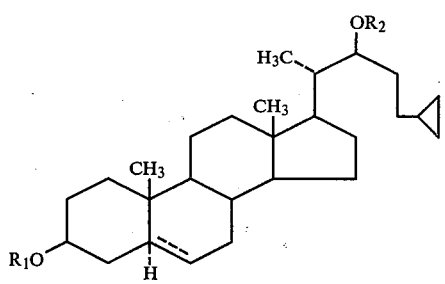

wherein the bond between $C_5$ and $C_6$ may be saturated or unsaturated; $R_1$ and $R_2$ may be the same or different and each represents hydrogen or an esterifying moiety such as 1-oxoalkyl frequently but not invariably Ω-substituted by carboxyl of the formula

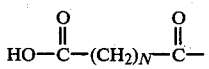

wherein N represents an integer from 1–6, preferably less than 4, namely, 2-carboxyl-1-oxoethyl, 3-carboxyl-1-oxopropyl and 4-carboxyl-1-oxobutyl.

A major risk in the development of atherosclerotic disease and associated clinical conditions is the level of circulating serum total cholesterol. As the level of serum total cholesterol rises above 180 mg/dl, the risk of atherosclerosis also increases. The low-density lipoproteins which are rich in cholesterol have been implicated as the primary vehicle for carrying cholesterol which will be deposited in tissues.

The major source of arterial cholesterol in the atherosclerotic patient appears to be of endogenous origin. A reduction in the rate of cholesterol biosynthesis will lead to a lowering of serum cholesterol levels. The rate limiting step in the biosynthesis of cholesterol is the enzymatic reduction of β-hydroxy-β-methylglutaryl Co A (HMG Co A) to mevalonic acid (MVA) by the enzyme HMG Co A reductase. Therefore, the regulation of cholesterol biosynthesis by supressing the activity of HMG Co A reductase will lead to a lowering of serum cholesterol levels.

Compounds of the present invention inhibit the activity of HMG Co A reductase. This type of activity should be particularly useful in controlling type II hypercholesterolemia, a inherited condition caused by an autosomal dominant mutation of a single gene locus [Brown and Goldstein, Science 191, 150 (1976).]

Reduction of HMG Co A reductase activity by the present compounds is demonstrated by the following assay. Male rats of the CD strain from Charles River weighing 180–250 g., initially being kept on a regular laboratory diet, are used. The rats are maintained in reverse light-cycle room for 3–6 days. 20,25-Diazacholesterol is administered for a total of 6 days at a dose of 5 mg/kg/day (IG). The last 3 days the test compound is administered along with the 20,25-diazacholesterol. Both compounds are given 2 hours prior to the test on last day. The rats are anesthetized with ether, sacrificed, and the livers removed. Liver microsomes are collected by differential centrifugation after homogenation. Liver microsomes are used as the source of the HMG Co A reductase. Details of the assay are reported in L. W. White and H. Rudney, Biochemistry 9, 2713 (1970); Brown et al., J. Biol. Chem. 248, 4731 (1973); and C. A. Edwards, Biochem. Biophys. Acts 409, 39 (1975). The percent change in formation of [$^{14}$C]-mevalonic acid from [$^{14}$C]-HMG Co A is used as a measure of enzyme activity for treated groups versus control groups of rats. If the treated groups have less activity, and the decrease is statistically significant at $P \leq 0.05$, the compound is rated active.

One of the preferred embodiments of this invention, 24-cyclopropylchol-5-ene-3β,22S-diol, was found to inhibit HMG Co A reductase activity in the foregoing test by 79 percent at 5 mg/kg (IG) and 32 percent at 0.5 mg/kg (IG).

The response to 24-cyclopropylchol-5-ene-3β,22S-diol set forth above is, of course, intended merely to illustrate this aspect of the instant invention and, accordingly, is not to be construed as either delimiting or exclusionary.

For therapeutic purposes, the compounds of this invention are ordinarily combined with one or more adjuvants appropriate to the indicated route of administration. If per os, they may be admixed with lactose, sucrose, starch powder, cellulose esters of alkanoic acids, cellulose alkyl ethers, talc, stearic acid, magnesium stearate, magnesium oxide, sodium and calcium salts of phosphoric and sulfuric acids, gelatin, acacia, sodium alginate, polyvinyl pyrrolidone, and/or polyfinyl alcohol, and thus tableted or encapsulated for convenient administration; alternatively, they may be dissolved or suspended in water or a comparably innocuous liquid. Parenteral administration may be effected via sterile fluid admixture with water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art: see, for example, F. W. Martin et al., "Remington's Pharmaceutical Sciences," 14 Ed., Merck Publishing Company, Eaton, Pa., 1965.

Appropriate dosages, in any given instance, of course, depend upon the nature and severity of the condition treated, the route of administration, and the species of mammal involved, including its size and any individual idiosyncrasies which obtain.

Preparation of the compounds of this invention proceeds variously as follows: 3β-acetoxy-22,24-bisnorchol-5-en-22-al [described in Chem. Pharm. Bull. (Japan), 26,3715 (1978)] of formula I

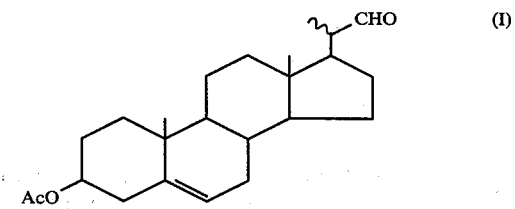

is contacted in cold tetrahydrofuran under nitrogen with a Grignard reagent of the formula

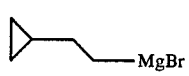 (II)

The Grignard reagent is prepared by treating cyclopropyl chloride with lithium in pentane at zero degrees Centrigrade to form cyclopropyl/lithium which in turn is treated with ethylene oxide to afford 2-cyclopropylethanol [described in *J. Am. Chem. Soc.* 81, 4894 (1959)] of formula
III. This alcohol is treated with triphenylphosphine in

 (III)

dimethylformamide in the presence of N-bromosuccinimide, which is added in portions over a 20–30 minute period at a reaction temperature of 20° C. to afford the corresponding alkyl bromide of formula IV. Reaction of

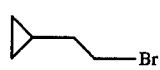 (IV)

the alkyl bromide with magnesium turnings in dry tetrahydrofuran provides the desired Grignard reagent of formula II.

From the reaction of the Grignard reagent and 3β-acetoxy-22,24-bisnorchol-5-en-22-al, the resultant acetoxy alcohol, a cholenediol derivative of formula VI

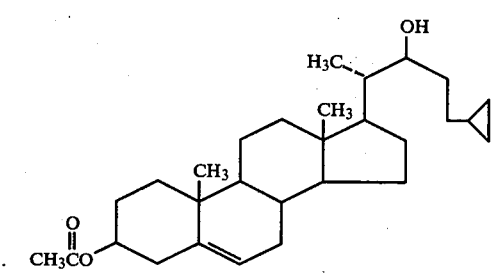 (VI)

is obtained. Removal of the acetate group with sodium hydroxide in methanol provides the free diol, of formula VII.

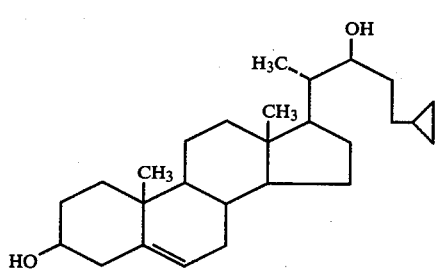 (VII)

Heating a compound of formula VII in pyridine with an alkanoic acid anhydride or chloride affords a mixture of esters of the invention having the formula

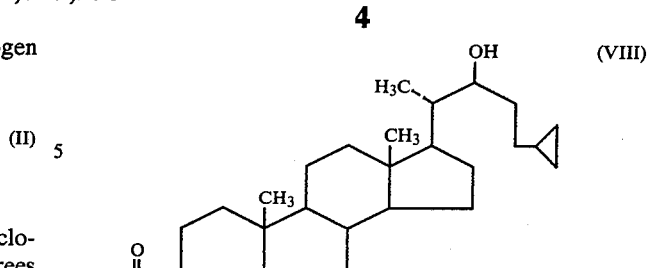 (VIII)

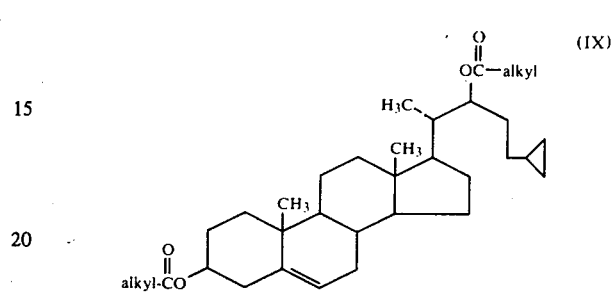 (IX)

separable via chromatography on silica gel, using methylbenzene and mixtures thereof with increasing amounts of ethyl acetate as developing solvents. Similarly, heating a compound of formula VII in pyridine with a methyl Ω-chloro-Ω-oxoalkanoate affords a mixture of mixed esters having the formula

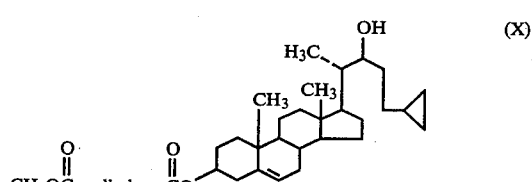 (X)

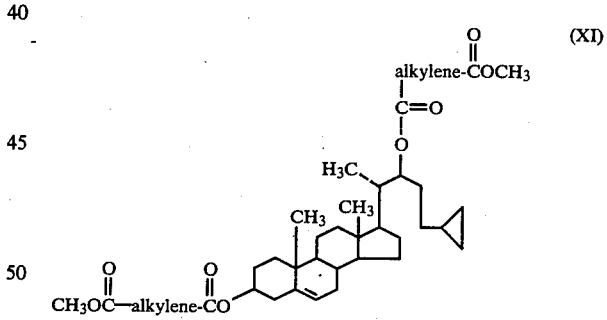 (XI)

separable via chromatography on silica gel as aforesaid; and heating an ester of formula X or XI with lithium iodide in pyridine, 2,6-dimethylpyridine, or 2,4,6-trimethylpyridine affords an ester of the invention having the formula

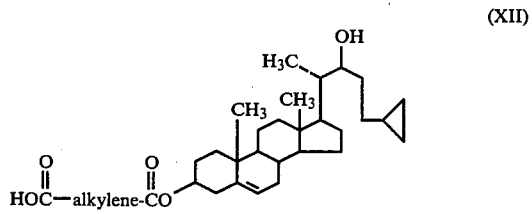 (XII)

-continued

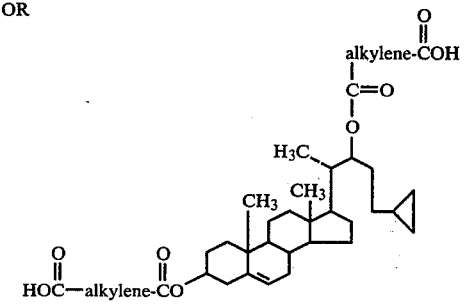
(XIII)

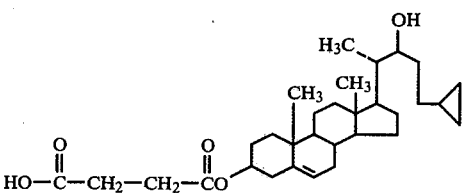
(XVI)

Heating the compound of formula XVI with succinic anhydride in pyridine-containing 4-dimethylaminopyridine affords the bis-hemisuccinate ester of formula XVII

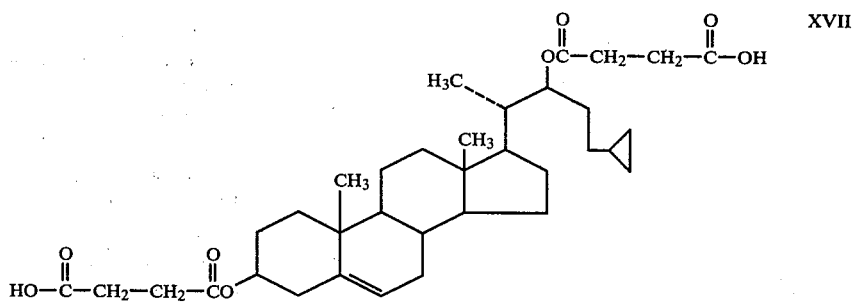
XVII respectively. Heating a compound of formula IX or XIII with sodium bicarbonate in aqueous ethanol affords a 22-ester of the invention having the following formula

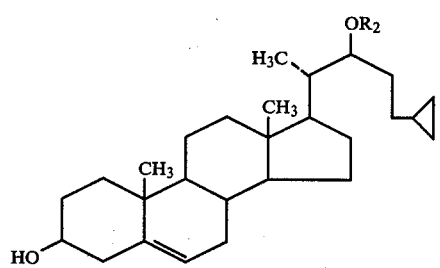
(XIV)

where R₂ represents 1-oxoalkyl or Ω-carboxy-1-oxoalkyl, respectively. Heating a compound of formula X in pyridine with an alkonic acid anhydride or chloride affords a mixed ester of the invention having the formula

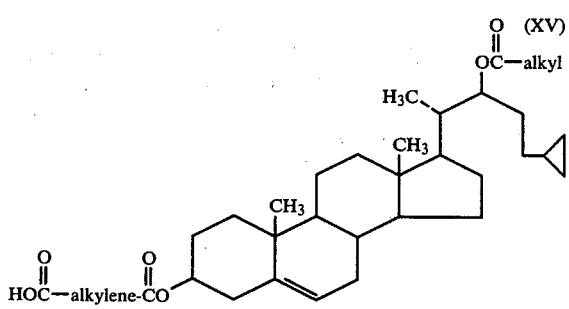
(XV)

Finally, treating the diol of formula VII with succinic anhydride in pyridine gives the hemisuccinate ester of formula XVI The olefinic bond of the diol is reduced with hydrogen over platinum to the dihydro sterol of formula XVII

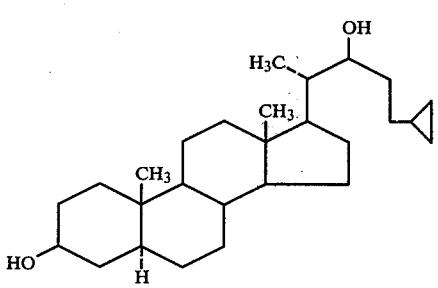
(XVIII)

The mono and diesters of formula VII can be formed with the compound of formula XVIII in an analogous manner.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees Centrigrade and relative amounts of materials in parts by weight, except as otherwise noted.

EXAMPLE 1

Preparation of 2-cyclopropylethylbromide

To 35 parts of 2-cyclopropylethanol in 250 parts of dimethylformamide (DMF) containing 110 parts of triphenylphosphine was added 75 parts of N-bromosuccinimide (NBS), in portions over a 20–30 minute period, using ice bath cooling to maintain a reaction temperature near 20° C. After addition was completed and the cooling bath was removed, the reaction mixture was stirred at room temperature for an additional 45 minutes to 1 hour. Excess NBS was destroyed with a few milliliters of methanol. After addition of 250 parts of water, the aqueous solution was extracted three times with N-pentane. The combined organic extracts were washed with 5 percent bicarbonate solution and with saturated NaCl solution and dried. Solvent was removed at room temperature under reduced pressure, giving a liquid which was distilled at atmospheric pressure (b.p. 129°–130°, lit. b.p. 129°–131°) [*Liebigs Ann. Chem.*, 759,132 (1971)] to give clean bromide having the formula

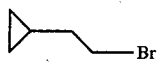

EXAMPLE 2

2-cyclopropylethyl magnesium bromide

To 2 parts of magnesium turnings in 40 parts of tetrahydrofuran (THF) 5 parts of 2-cyclopropylethyl bromide and a crystal or two of iodine. Upon warming the iodine, color faded and reaction commenced. After addition of another 20 parts of THF, another 5 parts of the alkyl bromide were added by dropwise addition, with the rate of addition and degree of cooling adjusted to maintain a gentle reflux. After addition was completed, the reaction mixture was stirred at room temperature for 30 minutes, then used directly for the subsequent reaction. The compound has the formula

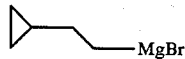

EXAMPLE 3

Preparation of 24-cyclopropylchol-5-ene-3β,22S-diol-3-acetate

The entire Grignard solution described in Example 2 was cooled to approximately −10° with a methanol/ice bath. To the cooled solution (maintained at −10° to 0° during addition) was added dropwise over a 5–10 minute period 10 parts of 3β-acetoxy-23,24-bisnorchal-5-en-22-al dissolved in 50 parts of THF. After addition was completed, the reaction mixture was stirred for about 10 minutes before quenching with saturated aqueous NH₄Cl. Diethyl ether was added, giving a separation of layers. The aqueous phase was separated and futher extracted with ether. All the organic layers were combined and washed twice with saturated NaCl solution and dried. The resultant mixture was filtered through a filter aid and the filtrate was concentrated to a white solid. Recrystallization from a dichloromethane-methanol mixture produced the purified product melting at about 179°–182°.

Analysis Calcd. for $C_{29}H_{46}O_3$: C, 78.68; H, 10.47. Found: C, 78.46; H, 10.86.

The compound has the formula

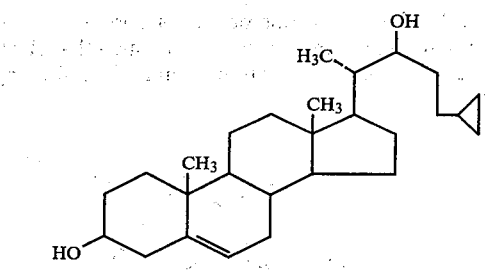

EXAMPLE 4

Preparation of 24-cyclopropylchol-5-ene-3β,22S-diol

To 12 parts of the acetate from Example 3 in 250 parts of methanol was added 50 parts of 5 percent aqueous sodium hydroxide. After being heated on a steam bath for about 15 minutes, the cloudy reaction mixture was clarified by rapid filtration. The cooled filtrate produced two crops of slightly impure product. Recrystallization from aqueous methanol produced the product which melts at about 174.5°–175°.

Analysis. Calcd. $C_{27}H_{44}O_2$: C, 80.94; H, 11.07. Found: C, 81.18; H, 11.42.

The compound has the formula

EXAMPLE 5

Preparation of 24-Cyclopropylchol-5-ene-3β,22S-diol 3 hydrogen butanedioate

To 5 parts of the diol from Example 4 in 50 parts of pyridine was added 5 parts of succinic anhydride. After being heated on a steam bath for 24 hours, the reaction mixture was cooled. Water and a small quantity of 1 N aqueous HCl were added, causing separation of an oil which, upon continuous stirring, solidified and was collected. The solid was recrystallized from aqueous methanol and then from ethyl acetate to give a pure product having a melting point of about 158°–160°.

Analysis: Calcd. for $C_{31}H_{48}O_5$: C, 74.36; H, 9.66. Found: C, 74.33; H, 9.73.

The compound has the formula

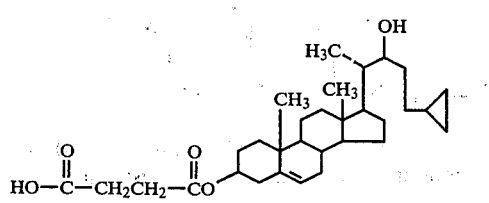

EXAMPLE 6

Preparation of 24-Cyclopropyl-5α-cholane-3β,22S-diol

To 4 parts of the diol from Example 4 in 300 parts of isopropyl alcohol was added 3.25 parts of PtO$_2$. The mixture was exposed to a hydrogen atmosphere at 60 psi and 60° until theoretical hydrogen uptake was attained. The catalyst was removed by filtration. Upon concentration, the filtrate produced a precipitate of pure crystalline dihydroxy sterol, melting at about 175°–178° C.

Analysis: Calcd. for C$_{27}$H$_{46}$O$_2$: C, 80.54; H, 11.52. Found: C, 80.20; H, 11.67.

The compound has the formula

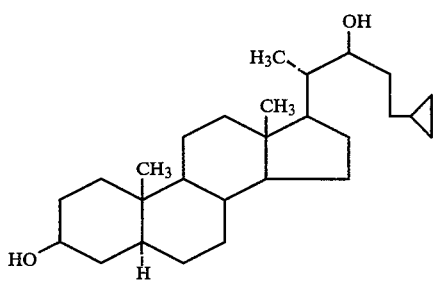

EXAMPLE 7

Preparation of 24-Cyclopropyl-chol-5-ene-3β,22-diol bis (hydrogen butanedioate)

To 4 parts of the ester from Example 5, in 40 parts of pyridine was added 2 parts of succinic anhydride and 1.4 parts of 4-dimethylaminopyridine, and the reaction mixture was heated at about 90° for six hours. The cooled reaction mixture was poured into a 5 percent HCl solution and this solution was extracted three times with ethyl acetate. The combined extracts were washed with saturated sodium chloride solution and dried over magnesium sulfate. The dried solution was then treated with activated charcoal and filtered. Solvent removed gave a solid residue which, upon recrystallization from aqueous methanol, affords the pure material represented by the formula

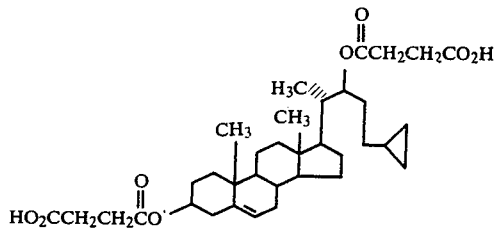

What is claimed is:

1. A compound of the formula

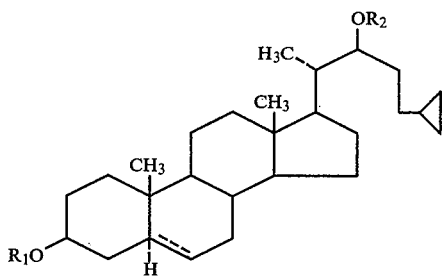

wherein the bond between C$_5$ to C$_6$ may be saturated or unsaturated;

R$_1$ and R$_2$ may be the same or different selected from the group consisting of a radical of the formula

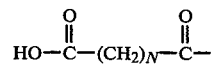

in which N represents an integer from 1–6 and hydrogen.

2. A compound of claim 1 which is 24-cyclopropyl-chol-5-ene-3β,22S-diol.
3. A compound of claim 1 which is 24-cyclopropyl-chol-5-ene-3β,22S-diol 3-acetate.
4. A compound of claim 1 which is 24-cyclopropyl-chol-5-ene-3β,22S-diol 3-hydrogen butanedioate.
5. A compound of claim 1 which is 24-cyclopropyl-chol-5-ene-3β,22S-diol bis(hydrogen butanedioate).
6. A compound of claim 1 which is 24-cyclopropyl-5α-cholane-3β,22S-diol.
7. A compound of claim 1 which is 24-cyclopropyl-5α-cholane-3β,22S-diol 3-hydrogen butanedioate.
8. A compound of claim 1 which is 24-cyclopropyl-5α-cholane-3,22S-diol bis(hydrogen butanedioate).

* * * * *